United States Patent [19]
Slater

[11] Patent Number: 5,395,341
[45] Date of Patent: Mar. 7, 1995

[54] ONE PIECE VESSEL DILATOR/CATHETER SHEATH INTRODUCER

[75] Inventor: Andrea T. Slater, Somerville, N.J.

[73] Assignee: Cordis Corporation, Miami Lakes, Fla.

[21] Appl. No.: 215,181

[22] Filed: Mar. 21, 1994

[51] Int. Cl.⁶ .......................................... A61M 5/178
[52] U.S. Cl. .................................... 604/164; 604/264
[58] Field of Search ............... 604/264, 265, 280, 281, 604/282, 165

[56] References Cited

U.S. PATENT DOCUMENTS

| | | |
|---|---|---|
| 4,000,739 | 1/1977 | Stevens . |
| 4,596,563 | 6/1986 | Pande ................................ 604/264 |
| 4,798,594 | 1/1989 | Hillstead . |
| 4,874,378 | 10/1989 | Hillstead . |
| 4,921,479 | 5/1990 | Grayzel . |
| 4,950,257 | 8/1990 | Hibbs et al. . |
| 4,994,027 | 2/1991 | Farrell . |
| 5,011,478 | 4/1991 | Cope . |
| 5,066,285 | 11/1991 | Hillstead . |
| 5,226,899 | 7/1993 | Lee et al. ............................ 604/282 |
| 5,281,677 | 1/1994 | Onwonaka et al. ............ 604/264 X |
| 5,292,311 | 3/1994 | Cope ................................... 604/165 |

*Primary Examiner*—John D. Yasko
*Attorney, Agent, or Firm*—Thomas R. Vigil

[57] ABSTRACT

The combined dilator/catheter sheath introducer is adapted to be mounted to an outlet from a housing of a catheter sheath introducer assembly. The introducer comprises an elongate tubular member including a proximal portion which is relatively stiff and which does not change shape with changes in temperature above and below the typical human body temperature and a tapered distal portion which is made of a material that has a temperature dependent memory and which changes shape when the temperature thereof is increased to body temperature so that the tapered distal portion can change from its first tapered shape to an expanded generally cylindrical shape with a diameter close to the diameter of the proximal portion.

5 Claims, 2 Drawing Sheets

ONE PIECE VESSEL DILATOR/CATHETER SHEATH INTRODUCER

BACKGROUND OF THE INVENTION

1. Field of the Invention

The present invention relates to a one piece dilator/catheter sheath introducer. More specifically, the present invention relates to a dilator/catheter sheath introducer which is mounted to an outwardly extending hub of a housing for a combination hemostasis valve and catheter sheath introducer assembly. The dilator/catheter sheath introducer is made of two materials, the proximal portion being made of a material which does not change shape with temperature, which has a constant diameter and which is mounted to said outlet hub and a distal portion which is tapered to form a dilator and which is made of a temperature sensitive material such that after its temperature is raised to the temperature of a human body, it expands to a diameter close to the diameter of the proximal portion.

2. Description of the Related Art Including Information Disclosed Under 37 C.F.R. 21211.97-1.99

Heretofore, hemostasis cannulas, hemostasis valves, dilators and catheter sheath introducers and assemblies thereof, including a hemostasis valve, have been proposed. Examples of these previously proposed catheter sheath introducers and assemblies, including a housing having a hemostasis valve and an entrance tube or sheath introducer are disclosed in the following patents.

| U.S. Pat. No. | Patentee |
| --- | --- |
| 4,000,739 | Stevens |
| 4,798,594 | Hillstead |
| 4,874,378 | Hillstead |
| 4,921,479 | Grayzel |
| 4,950,257 | Hibbs et al. |
| 4,994,027 | Farrell |
| 5,011,478 | Cope |

The Stevens U.S. Pat. No. 4,000,739 discloses a hemostasis cannula having first and second gasket seals mounted to a housing for receiving a catheter. The housing has connected to an outlet end thereof, a body entrance tube made of a plastic material, such as high density polyethylene which is adapted to be inserted into a puncture through tissue to a blood vessel after the puncture has been dilated by a dilator.

The Hillstead U.S. Pat. No. 4,798,594 discloses a hemostasis valve mounted in a housing of a catheter introducer and includes a cannula portion of a catheter sheath introducer which permits a catheter to pass therethrough.

The Hillstead U.S. Pat. No. 4,874,378 discloses a catheter sheath introducer having a molded plastic cannula extending from a ball that is mounted in a socket at a distal end of a housing of a catheter sheath introducer assembly.

The Grayzel U.S. Pat. No. 4,921,479 discloses a catheter sheath with a longitudinal seam. The sheath is made of an expandable material that is fabricated from a semi-stiff plastic with memory and is formed in a tubular configuration with a longitudinal slit or non-joined seam extending along the entire length of the sheath so that, where the tubular structure with the slit is coiled about its longitudinal axis, the tubular wall thereof overlaps itself in its native state so as to form a cone. Then, on exertion of an internal force directed outward, the tubular sheath enlarges its effective diameter by uncoiling, effected such as by inserting a catheter through the coiled tubular sheath. The memory inherent in the material of the sheath keeps the wall of the sheath snugly around the catheter to afford guidance of the catheter into a blood vessel such that the coiled sheath forms both a dilator and a catheter introducer.

The Hibbs et al. U.S. Pat. No. 4,950,257 discloses a catheter introducer including a tubular sheath with a relatively rigid tubular body and a soft flexible tubular tip extending therefrom.

The Farrell U.S. Pat. No. 4,994,027 discloses a dilator sleeve which may be moved along a guide wire until the guide wire is inserted into a vessel. Thereafter, a sheath is moved along the guide wire and over the dilator sleeve so that, upon removal of the dilator sleeve from the guide wire, the sheath may be compressed to prevent escape of fluid through the sheath and a cannula may be inserted into the sheath along the guide wire. A succession of dilator sleeves in a telescoping arrangement can be inserted into the puncture hole to the vessel to dilate the puncture hole.

The Cope U.S. Pat. No. 5,011,478 discloses a recessed dilator-sheath assembly. The distal end of a sheath portion of a catheter sheath introducer is embedded in the proximal end of the dilator. This construction permits the sheath to be inserted into the body with a minimum of trauma to the patient and also permits easy removal of the sheath from the dilator.

The Hillstead U.S. Pat. No. 5,066,285 discloses a catheter introducer sheath made of expanded polytetrafluoroethylene which is used with a dilator unit.

SUMMARY OF THE INVENTION

According to the present invention there is provided a combined dilator/catheter sheath introducer which is adapted to be mounted to an outlet from a housing of a catheter sheath introducer assembly. The combined dilator/sheath introducer comprises an elongate tubular member including a proximal portion which is relatively stiff and which does not change shape with changes in temperature above and below the typical human body temperature and a tapered distal portion which is made of a material that has a temperature dependent memory and which expands when the temperature thereof is increased to body temperature so that upon increasing temperature of the distal end to body temperature the tapered distal portion changes from its first tapered shape to a second generally cylindrical shape with a diameter close to the diameter of the proximal portion whereby a guidewire for a guidewire and catheter can be inserted into the proximal portion of the dilator/introducer and pass out of the distal portion of the dilator/introducer.

DESCRIPTION OF THE PREFERRED EMBODIMENT(S)

Figures 1, 2:
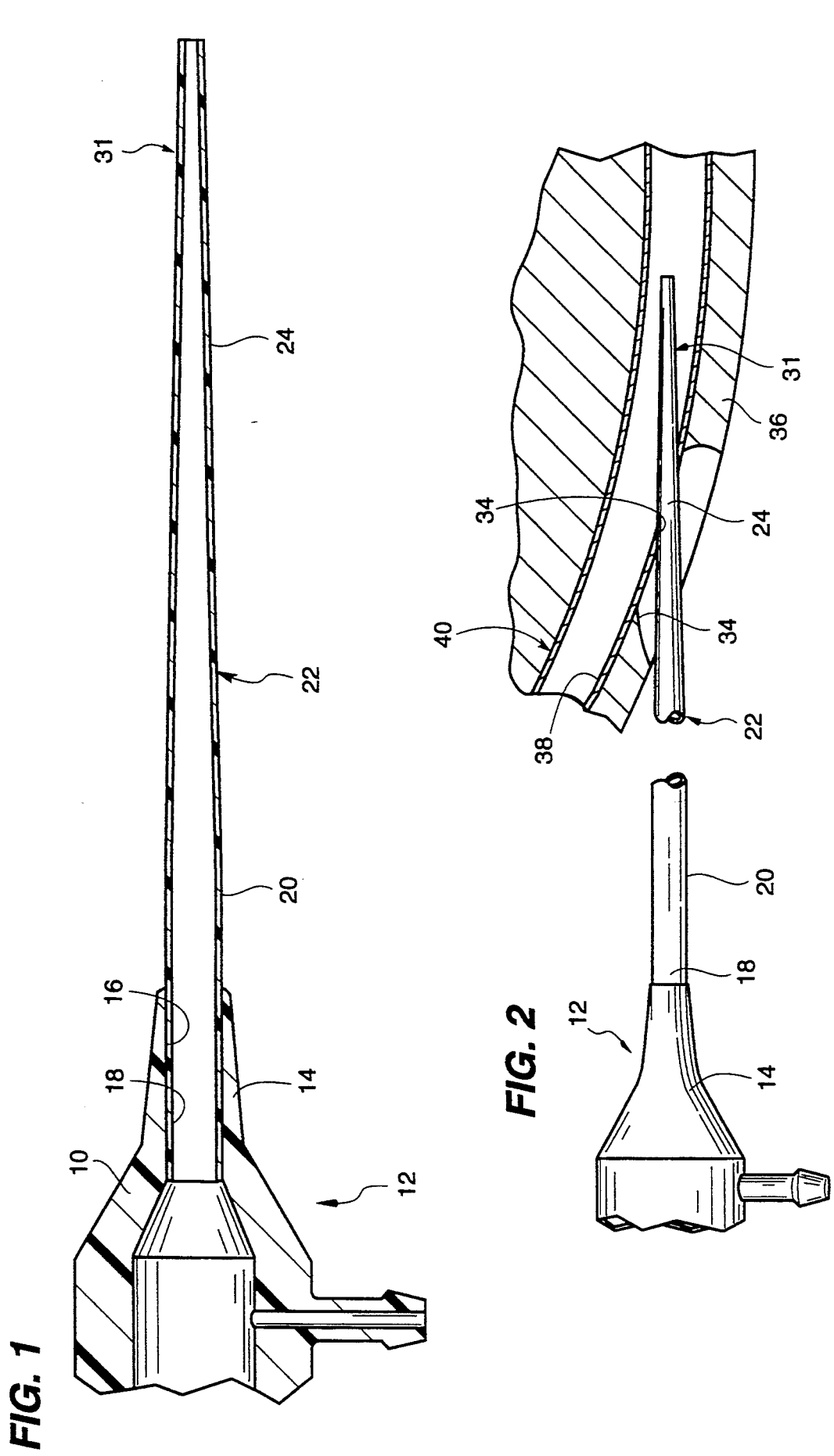
FIG. 1 is a longitudinal view of the dilator/catheter sheath introducer constructed according to the teachings of the present invention mounted to an outlet hub of a housing of a sheath introducer assembly, the proximal portion of which is broken away.
FIG. 2 is a side elevational view with portions broken away of the dilator/catheter sheath introducer of the present invention being inserted through a puncture opening or hole to a blood vessel.

Referring now to FIG. 1 in greater detail, there is illustrated therein a conventional housing 10 of a catheter sheath introducer assembly 12 with a proximal portion of the housing 10 omitted and showing the housing 10 having a tapered outlet hub 14. The tapered outlet hub 14 has an inner bore 16 which receives a proximal end 18 of a proximal portion 20 of a dilator/catheter sheath introducer 22 constructed according to the teachings of the present invention. Fixed to the proximal portion, such as by fusing or heat butt welding, is a tapered distal portion 24 of the dilator/catheter sheath introducer 22.

According to the teachings of the present invention, the proximal portion 20 of the combined dilator/catheter sheath introducer 22 is made of a material such as polyethylene or polyurethane which is relatively stiff and which does not change shape with changes in temperature above and below the typical human body temperature of 98.2 F°.

Figure 3:
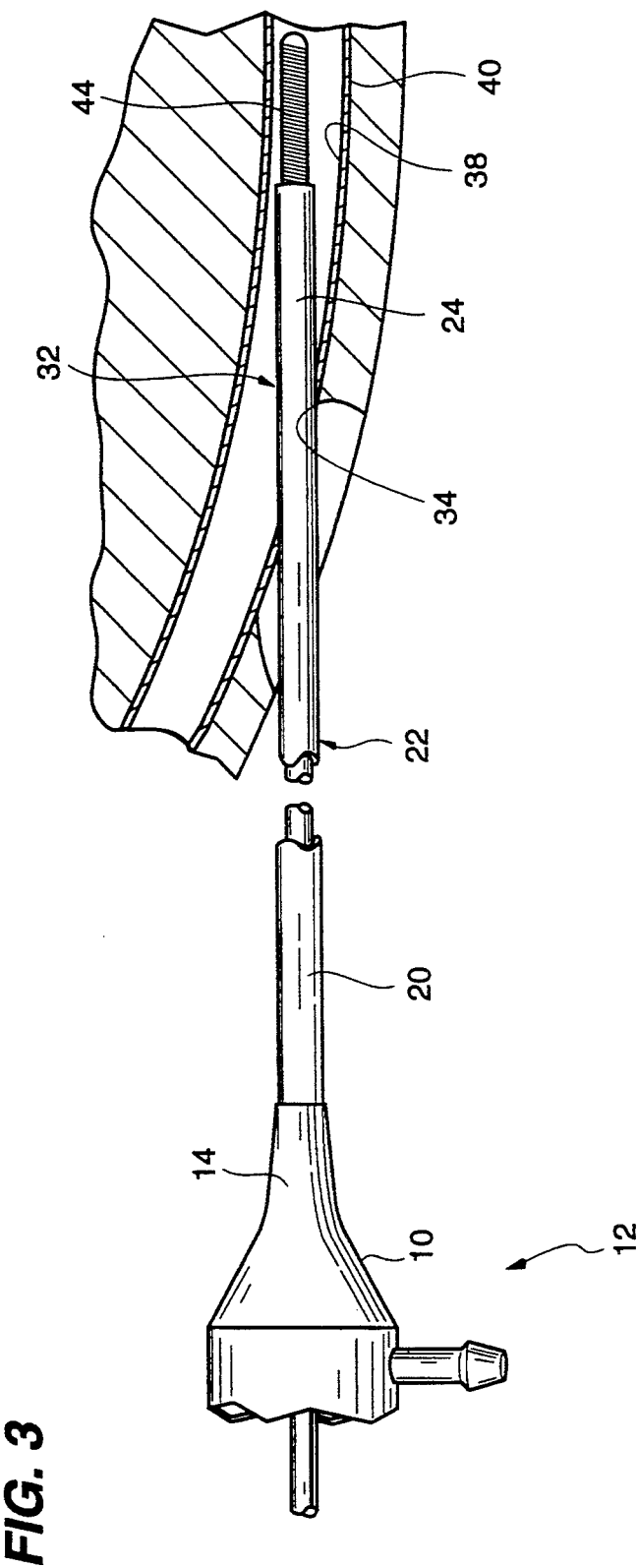
FIG. 3 is a longitudinal view with portions broken away of the dilator/catheter sheath introducer, similar to the view shown in FIG. 2, but after the dilator/catheter sheath introducer has been in place for a period of time sufficient to allow the temperature of the dilator/catheter sheath introducer to be raised to body temperature thereby causing the distal portion of the dilator/catheter sheath introducer to increase its diameter to close to the diameter of the proximal portion thereof.

Further according to the teachings of the present invention, the distal portion 24 of the combined dilator/catheter sheath introducer 22 is made of a material such as polyurethane or nitinol which has a temperature dependent memory and which changes shape when the temperature thereof is increased to body temperature from a first tapered shape 31, as shown in FIGS. 1 and 2, to an expanded shape 32, as shown in FIG. 3.

As best shown in FIG. 2 a puncture opening 34 is formed through tissue 36 and through a wall 38 of a blood vessel 40. After the puncture opening 34 has been made, the distal portion 24 with the tapered shape 31 is inserted through the wall 38 of, and into, the blood vessel 40.

Then as shown in FIG. 3, after the distal portion 24 with the taper shaped 31 has been pushed into the vessel 40 to dilate the puncture opening 34, the distal portion 24 is heated by body temperature and expands to the shape 31 shown in FIG. 3. At this point in time, a guidewire 44 or catheter and guidewire 44 can be inserted into the vessel 40 through the now expanded dilator/sheath introducer 22.

From the foregoing description it will be apparent that the dilator/catheter sheath introducer 22 of the present invention has a number of advantages some of which have been described above and others of which are inherent in the invention. In particular, by having a shape changing distal portion 24 of a dilator/catheter sheath introducer 22, the need for a separate dilator and a separate sheath introducer is eliminated. Also the step or procedure of exchanging a dilator with a catheter sheath introducer is eliminated in the use of the combined dilator/catheter sheath introducer 22.

I claim:

1. A combined dilator/catheter sheath introducer which is adapted to be mounted to an outlet from a housing of a catheter sheath introducer assembly, said combined dilator/catheter sheath introducer comprising: an elongate tubular member including a proximal portion which is relatively stiff and which does not change shape with changes in temperature above and below the typical human body temperature and a tapered distal portion which is made of a material that has a temperature dependent memory and which expands when the temperature thereof is increased to body temperature so that upon increasing the temperature of the distal end to body temperature said tapered distal portion changes from its first tapered shape to a second expanded generally cylindrical shape with a diameter close to the diameter of the proximal portion whereby a guidewire or guidewire and catheter can be inserted into said proximal portion of said dilator/introducer and pass out of said distal portion of said dilator/introducer.

2. The combined dilator/catheter sheath introducer of claim 1 wherein said proximal portion of said sheath introducer is made of polyethylene or polyurethane.

3. The combined dilator/catheter sheath introducer of claim 1 wherein said distal portion of said combined dilator/catheter sheath introducer is made of polyurethane or nitinol.

4. The combined dilator/catheter sheath introducer of claim 1 wherein said distal portion is fused or welded to said proximal portion.

5. A method for dilating a puncture hole to a blood vessel and thereafter introducing a guidewire and or catheter into the blood vessel using a combined dilator/catheter sheath introducer which is adapted to be mounted to an outlet from a housing of a catheter sheath introducer assembly, said combined dilator/catheter sheath introducer comprising: an elongate tubular member including a proximal portion which is relatively stiff and which does not change shape with changes in temperature above and below the typical human body temperature and a tapered distal portion which is made of a material that has a temperature dependent memory and which expands when the temperature thereof is increased to body temperature so that upon increasing the temperature of the distal portion to body temperature said tapered distal portion changes from its first tapered shape to a second expanded generally cylindrical shape with a diameter close to the diameter of the proximal portion, said method comprising the steps of:

inserting the tapered distal portion of the combined dilator/catheter sheath introducer into a puncture hole through tissue of a body and through a hole in a wall of a vessel into the vessel;

slowly moving the dilator/catheter sheath introducer into the blood vessel to dilate the puncture hole and the hole through the wall of the blood vessel;

allowing the dilator/catheter sheath introducer to increase in temperature to the temperature of the body thereby to cause the distal portion of the dilator/catheter sheath introducer to expand; and introducing a guidewire or a guidewire and a catheter into the proximal portion of the dilator/catheter sheath introducer, through the dilator/catheter sheath introducer now having an expanded-in-diameter distal portion, out of the distal portion of the dilator/catheter sheath introducer and into the blood vessel.

* * * * *